(12) United States Patent
Harvard

(10) Patent No.: US 8,493,559 B2
(45) Date of Patent: Jul. 23, 2013

(54) CUVETTE

(76) Inventor: Trevor Harvard, Whitinsville, MA (US)

( * ) Notice: Subject to any disclaimer, the term of this patent is extended or adjusted under 35 U.S.C. 154(b) by 141 days.

(21) Appl. No.: 12/722,605

(22) Filed: Mar. 12, 2010

(65) Prior Publication Data
US 2010/0238436 A1 Sep. 23, 2010

Related U.S. Application Data

(60) Provisional application No. 61/160,789, filed on Mar. 17, 2009.

(51) Int. Cl.
*G01N 1/10* (2006.01)
(52) U.S. Cl.
USPC .......................................... 356/246; 356/440
(58) Field of Classification Search
USPC .................. 356/244–246, 335–343, 432–440
See application file for complete search history.

(56) References Cited

U.S. PATENT DOCUMENTS

| | | | | |
|---|---|---|---|---|
| 4,227,810 A | * | 10/1980 | Sandrock et al. | 356/246 |
| 4,696,798 A | * | 9/1987 | Timgren | 356/246 |
| 5,000,922 A | | 3/1991 | Turpen | |
| 5,571,479 A | * | 11/1996 | Koch | 422/549 |
| 6,249,345 B1 | | 6/2001 | Kraack et al. | |
| 7,138,091 B2 | * | 11/2006 | Lee et al. | 422/554 |
| 2003/0218128 A1 | | 11/2003 | Schulz | |
| 2007/0019189 A1 | * | 1/2007 | Marsteller et al. | 356/246 |
| 2010/0075317 A1 | * | 3/2010 | Schneider et al. | 435/6 |
| 2010/0182597 A1 | * | 7/2010 | Sahiri et al. | 356/246 |

OTHER PUBLICATIONS

International Search Report mailed Nov. 4, 2010 in corresponding International Patent Application No. PCT/US2010/027290.

* cited by examiner

*Primary Examiner* — Hoa Pham
(74) *Attorney, Agent, or Firm* — Anderson Gorecki & Rouille LLP

(57) ABSTRACT

A cuvette is shaped cylindrically at one end in order to be placed in a standard microfuge and is designed to specifically remove unwanted contaminates by centrifugation. The lower part of the cuvette is shaped substantially smaller to collect liquids for direct analysis and has a shape that will conform to a variety of spectrophotometers for the measurement of the absorption of irradiation and at times the subsequent scattering of light from the liquid samples which at least in the regions of the windows or desired shape is of a transparent plastic or glass with an inner space. The upper opening of the cuvette is for filling and removing sample fluid and sample preparation in a centrifuge and the lower part projects downwards towards the floor of the measuring chamber and which comprises a smaller cross section than the upper part. A cuvette holder is designed to conform to the shape of the cuvette with an outer surface to conform to the specific measuring device.

20 Claims, 4 Drawing Sheets

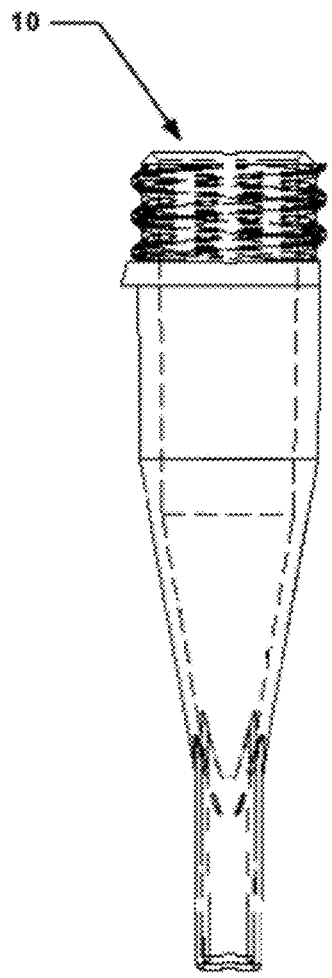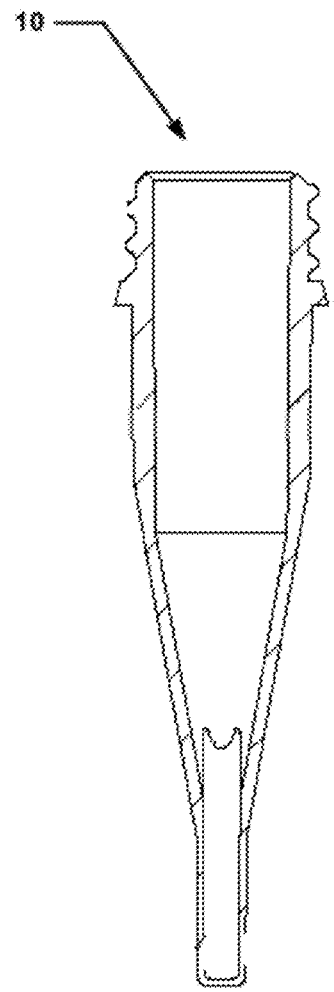
FIGURE 1B  FIGURE 1C

CUVETTE

CROSS REFERENCE TO RELATED APPLICATIONS

The present application claims the benefit of U.S. Provisional Patent Application No. 61/160,789, filed on Mar. 17, 2009, which is incorporated herein by reference in its entirety.

BACKGROUND

Cuvettes are typically used for measuring the absorption of irradiation in liquid samples. One example of a cuvette is described in U.S. Pat. No. 6,249,345 (hereinafter the '345 patent). In the '345 patent the cuvette has a generally rectangular box-like shape including a pair of windows opposite each other through which light is passed into the cuvette which has a fluid sample stored therein.

SUMMARY

Conventional mechanisms such as those explained above suffer from a variety of deficiencies. One such deficiency is that conventional cuvettes are not useful or easily adapted to fit within microfuges or centrifuges while also being used being used for the measuring of absorption of irradiation and/or scattering of light in the liquid samples disposed within the cuvette.

Embodiments of the invention significantly overcome such deficiencies and provide mechanisms and techniques that provide a cuvette wherein the upper body is designed to be inserted into a microfuge or standard centrifuge and the lower portion of the cuvette is designed to fit into any commercial spectrophotometers, dynamic light scattering devices (Photon Correlation Spectrometers) or a Goniometric Instrument or Nephalometer.

Note that each of the different features, techniques, configurations, etc. discussed in this disclosure can be executed independently or in combination. Accordingly, the present invention can be embodied and viewed in many different ways. Also, note that this summary section herein does not specify every embodiment and/or incrementally novel aspect of the present disclosure or claimed invention. Instead, this summary only provides a preliminary discussion of different embodiments and corresponding points of novelty over conventional techniques. For additional details, elements, and/or possible perspectives (permutations) of the invention, the reader is directed to the Detailed Description section and corresponding figures of the present disclosure as further discussed below.

BRIEF DESCRIPTION OF THE DRAWINGS

The foregoing will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 1B shows a side view of the cuvette in accordance with embodiments of the present invention;

FIG. 1C shows a cut-away view of the cuvette respectively in accordance with embodiments of the present invention;

DETAILED DESCRIPTION

The invention relates to a cuvette that enables liquid sample preparation in a microfuge or standard centrifuge where the lower portion is designed with the optical properties required for measuring the absorption of irradiation and/or scattering of light in liquid samples. The main objective of this device is to prepare samples for light scattering analysis in commercial static and dynamic light scattering instruments. There also exists applications in other types of spectroscopic devices, e.g., Ultra Violet, Fluorescence, Fluorescence Correlation Spectroscopy. The optically clear portion of the cuvette is generally square or rectangular in the portion of spectroscopic observation. There is also provision for other shapes other than square and rectangular, including, bur not limited to, rhomboid, triangular and pentagons up to the infinite number of windows that would be defined as a circular shape.

There is also the requirement for a cuvette holder having an outer portion that is shaped to fit commercially available measuring devices and an inner portion that is shaped to snugly accommodate the cuvette shape. There is the provision for a cover to be removably attached to the cuvette. An insert can be used to aid purification of the liquid sample inside the cuvette. The insert will fit into the cylindrical upper portion of the cuvette and will contain additional filtration elements or media to remove contaminates or retain portions of the sample.

The cuvette can be used in clinical diagnostics where a combination of the above components with the cuvette could be used for the analysis of plasma samples and pathogens. It is also designed for use in, but not limited to, environmental analysis, polymer analysis, bacteria analysis, virus analysis, microphage analysis, protein analysis, antibodies, gold particles and any defined nano-particles.

Figure 1A:
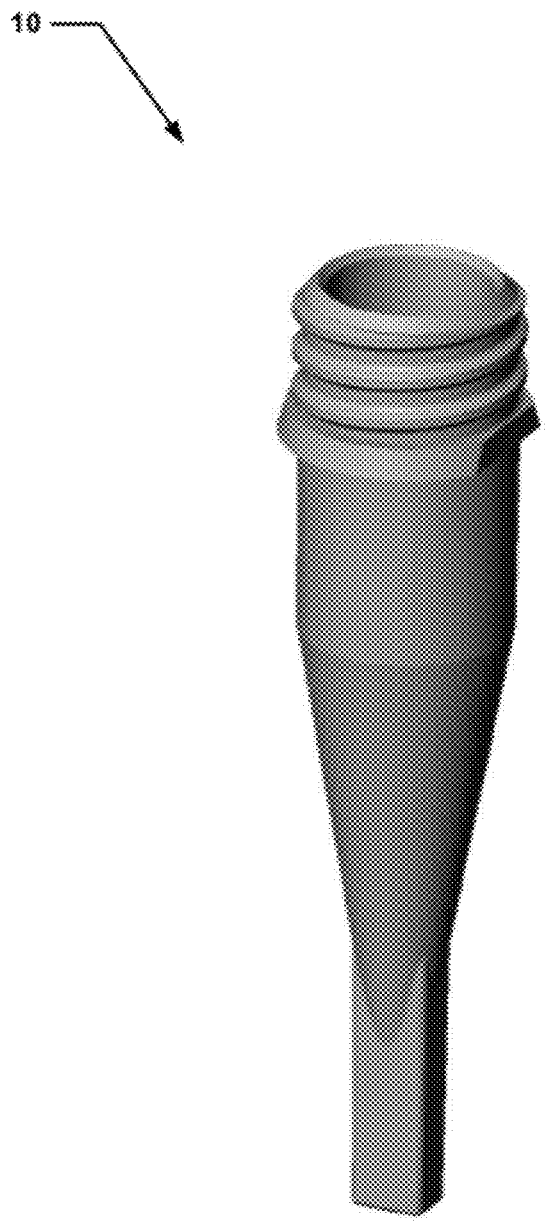
FIG. 1A shows an isometric view of a cuvette in accordance with embodiments of the present invention.

Referring to FIGS. 1A-1C, a new type of cuvette 10 is shown wherein the upper body 12 of the cuvette 10 has a substantially cylindrical shape and is designed to be inserted into a microfuge or standard centrifuge. The lower portion 14 of the cuvette 10 has a generally rectangular shape and is designed to fit into any commercial spectrophotometers, dynamic light scattering devices (Photon Correlation Spectrometers) or a Goniometric Instrument or Nephalometer or the like. Cuvette 10 further includes a threaded part 16 of the opening for attachment of a cover or the like.

The cuvette 10 has two pairs of planar-parallel windows 18 provided in the lower body 14 which lie opposite one another, wherein a distance of the windows of one pair is different from a distance of the windows of another pair in order to make available various layers of thickness of the sample fluid for measurement of samples.

In a particular embodiment, a content capacity of the lower body of the cuvette is about 50 microliters. In another particular embodiment, a ratio of the distances between the parallel windows of the two parts is 2:3. The distance between the windows of one of the two pairs of planar-parallel windows is approximately between one and three millimeters. The cuvette, at least in a region of the windows, is UV-transparent. Further, at least a portion of the lower body is transparent to visible light. The cuvette may also include at least one shielding against at least one of foreign light, stray light and a screen. The cuvette may be manufactured from a material that has been developed to work with any wavelength defined to operate within a measuring device.

Figure 2A:
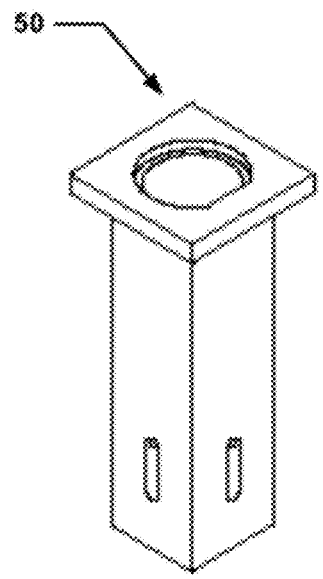
FIG. 2A shows an isometric view of a cuvette holder, in accordance with embodiments of the present invention.
Figure 2B:
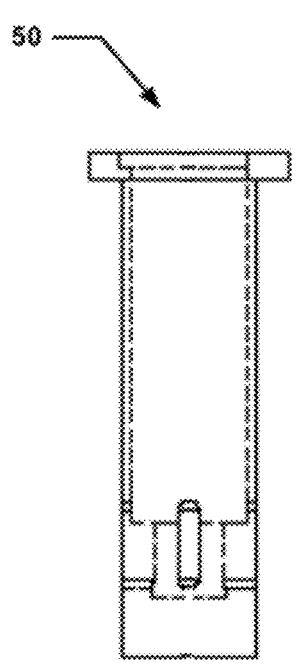
FIG. 2B shows a side view of the cuvette holder in accordance with embodiments of the present invention.
Figure 2C:
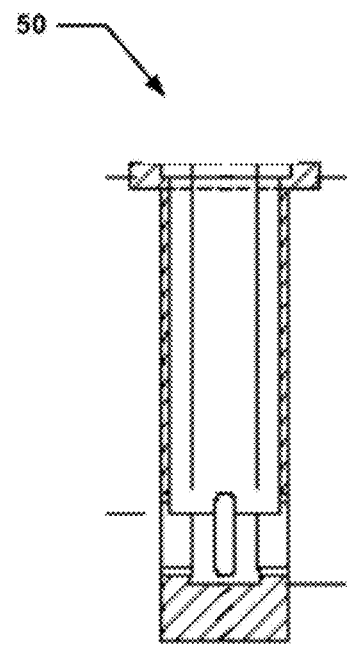
FIG. 2C shows a cut-away view of the cuvette holder respectively in accordance with embodiments of the present invention.

Referring now to FIGS. 2A-2C, a cuvette holder 50 is shown. Holder 50 is designed for storing cuvette 10 therein. Holder 50 comprises a generally rectangular shaped device having a collar 52 on an upper end thereof and wherein an opening 54 is defined therein. A cuvette is placed into opening of the holder 50 and is supported therein. The holder 50 also has a pair of openings 56 and 58 in opposite sidewalls for allowing light to pass therethrough for testing a sample within a cuvette.

Figure 3A:
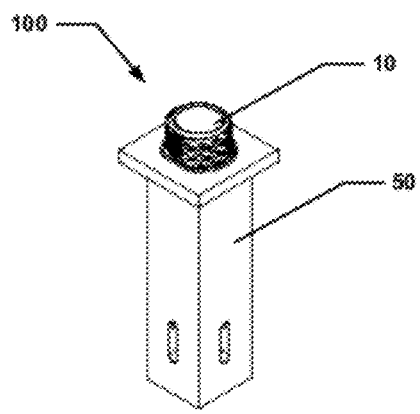
FIG. 3A shows an isometric view of a cuvette and holder assembly in accordance with embodiments of the present invention.
Figure 3B:
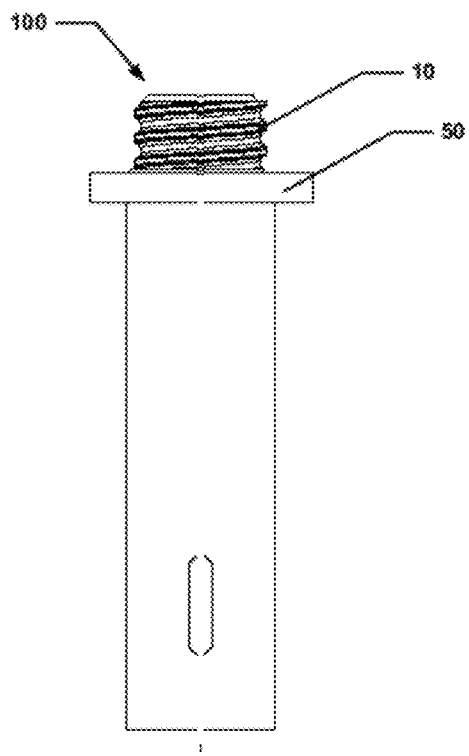
FIG. 3B shows a side view of the cuvette and holder assembly in accordance with embodiments of the present invention.
Figure 3C:
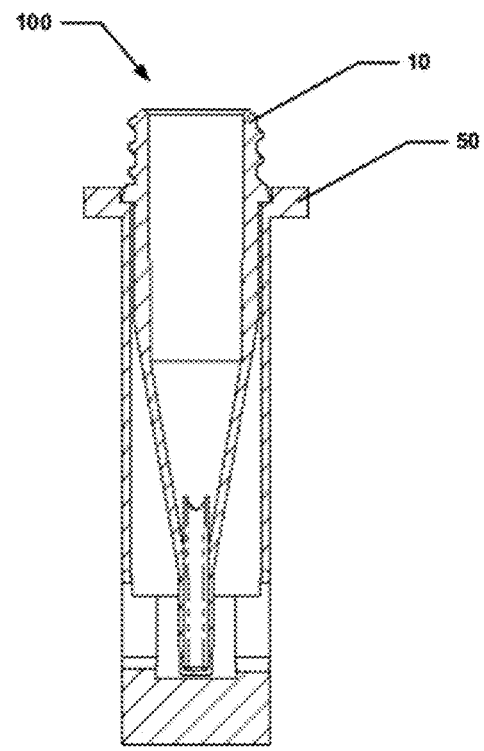
FIG. 3C shows a cut-away view of the cuvette and holder assembly respectively in accordance with embodiments of the present invention.

Referring now to FIGS. 3A-3C, a cuvette and holder assembly 100 is shown. Here, a cuvette 10 is placed within the opening of holder 50. The openings 56 and 58 in the sidewalls of the holder 50 are aligned with the windows 18 in the cuvette 10, such that light can be used to analyze a sample within the cuvette.

As described above, cuvette for measuring absorption or scattering due to irradiation of liquid probes is presented and described. The cuvette features a substantially conical upper body having an inner space for receiving a sample liquid probe, wherein an inner space is formed in the upper body, said upper body having an opening for filling and removing sample fluid. The cuvette further includes a smaller, essentially box-shaped lower body for the measuring volume connected with the upper body via a transition, wherein the cuvette has two pairs of planar-parallel windows provided in the lower body which lie opposite one another, wherein a distance of the windows of one pair is different from a distance of the windows of another pair in order to make available various layers of thickness of the sample fluid for measurement of samples.

Unless otherwise stated, use of the word "substantially" may be construed to include a precise relationship, condition, arrangement, orientation, and/or other characteristic, and deviations thereof as understood by one of ordinary skill in the art, to the extent that such deviations do not materially affect the disclosed methods and systems.

Throughout the entirety of the present disclosure, use of the articles "a" or "an" to modify a noun may be understood to be used for convenience and to include one, or more than one of the modified noun, unless otherwise specifically stated.

Elements, components, modules, and/or parts thereof that are described and/or otherwise portrayed through the figures to communicate with, be associated with, and/or be based on, something else, may be understood to so communicate, be associated with, and or be based on in a direct and/or indirect manner, unless otherwise stipulated herein.

Although the methods and systems have been described relative to a specific embodiment thereof, they are not so limited. Obviously many modifications and variations may become apparent in light of the above teachings. Many additional changes in the details, materials, and arrangement of parts, herein described and illustrated, may be made by those skilled in the art.

Having described preferred embodiments of the invention it will now become apparent to those of ordinary skill in the art that other embodiments incorporating these concepts may be used. Accordingly, it is submitted that that the invention should not be limited to the described embodiments but rather should be limited only by the spirit and scope of the appended claims.

What is claimed is:

1. A cuvette for measuring absorption or scattering due to irradiation of liquid probes, said cuvette comprising:
    a substantially conical upper body having an inner space for receiving a sample liquid probe, wherein an inner space is formed in the upper body, said upper body having an opening for filling and removing sample fluid, and in a smaller, essentially box-shaped lower body for the measuring volume connected with the upper body via a transition, wherein the cuvette has two pairs of planar-parallel windows provided in the lower body which lie opposite one another, wherein a distance of the windows of one pair is different from a distance of the windows of another pair in order to make available various layers of thickness of the sample fluid for measurement of samples.

2. The cuvette of claim 1 further comprising an insert disposed inside said cuvette in order to contain media or filtration to remove specific contaminates during centrifugation.

3. The cuvette of claim 1 wherein a content capacity of the lower body is about 50 microliters.

4. The cuvette of claim 1, wherein a ratio of the distances between the parallel windows of the two parts is 2:3.

5. The cuvette of claim 1, wherein the distance between the windows of one of the two pairs of planar-parallel windows is 3 millimeters.

6. The cuvette of claim 1, wherein the distance between the windows of another of the two pairs of planar-parallel windows is 2 millimeters.

7. The cuvette of claim 1, wherein the distance between the windows of another of the two pairs of planar-parallel windows is 1 millimeter.

8. The cuvette of claim 1, wherein the cuvette, at least in a region of the windows, is UV-transparent.

9. The cuvette of claim 1, wherein at least a portion of the lower body is transparent to visible light.

10. The cuvette of claim 1, further comprising at least one shielding against at least one of foreign light, stray light and a screen.

11. The cuvette of claim 1 wherein said substantially conical upper body is adapted for use in a centrifuge device and wherein said box-shaped lower body is adapted for use in a spectrophotometer device.

12. A cuvette holder, comprising:
    a generally rectangular body defining a conical space therein, the body having an opening along a top surface thereof, said opening for fitting a cuvette having a substantially conical upper body therein and wherein said cuvette holder includes a pair of openings that align with windows of a cuvette when a cuvette is inserted within said cuvette holder.

13. The cuvette holder of claim 12 further comprising a collar disposed along a top surface of said body.

14. An assembly comprising:
    a cuvette comprising a substantially conical upper body having an inner space for receiving a sample liquid probe, wherein an inner space is formed in the upper body, said upper body having an opening for filling and removing sample fluid, and in a smaller, essentially box-shaped lower body for the measuring volume connected with the upper body via a transition, wherein the cuvette has two pairs of planar-parallel windows provided in the lower body which lie opposite one another, wherein a distance of the windows of one pair is different from a distance of the windows of another pair in order to make available various layers of thickness of the sample fluid for measurement of samples;

a cuvette holder comprising a generally rectangular body defining a conical space therein, the body having an opening along a top surface thereof, said opening for fitting a cuvette having a substantially conical upper body therein and wherein said cuvette holder includes a pair of openings which align with windows of a cuvette when a cuvette is inserted within said cuvette holder; and wherein said cuvette is disposed within said cuvette holder.

15. The cuvette of claim 14, wherein a ratio of the distances between the parallel windows of the two parts is 2:3.

16. The cuvette of claim 14, wherein the distance between the windows of one of the two pairs of planar-parallel windows is 3 millimeters.

17. The cuvette of claim 14, wherein the distance between the windows of another of the two pairs of planar-parallel windows is 2 millimeters.

18. The cuvette of claim 14, wherein the cuvette, at least in a region of the windows, is UV-transparent.

19. The cuvette of claim 14, wherein at least a portion of the lower body is transparent to visible light.

20. The cuvette holder of claim 14 further comprising a collar disposed along a top surface of said body.

* * * * *